(12) United States Patent
Dalena et al.

(10) Patent No.: US 12,318,558 B2
(45) Date of Patent: *Jun. 3, 2025

(54) CATHETER INSERTION DEVICE WITH TIP PROTECTOR HOUSING

(71) Applicant: SMITHS MEDICAL ASD, INC., Plymouth, MN (US)

(72) Inventors: Michele E Dalena, Plymouth, MN (US); Kathryn Felicito, Plymouth, MN (US); David J Goral, Plymouth, MN (US); Jay T Breindel, Plymouth, MN (US); Christopher Roehl, Plymouth, MN (US); Harsh D Chheda, Plymouth, MN (US); Walton A Norfleet, Plymouth, MN (US)

(73) Assignee: ICU Medical, Inc., San Clemente, CA (US)

( * ) Notice: Subject to any disclaimer, the term of this patent is extended or adjusted under 35 U.S.C. 154(b) by 271 days.

This patent is subject to a terminal disclaimer.

(21) Appl. No.: 17/514,438

(22) Filed: Oct. 29, 2021

(65) Prior Publication Data
US 2022/0047852 A1    Feb. 17, 2022

Related U.S. Application Data

(63) Continuation of application No. 16/486,108, filed as application No. PCT/US2018/021135 on Mar. 6, 2018, now Pat. No. 11,185,668.
(Continued)

(51) Int. Cl.
*A61M 25/06*    (2006.01)
*A61M 25/00*    (2006.01)

(52) U.S. Cl.
CPC .... *A61M 25/0618* (2013.01); *A61M 25/0097* (2013.01); *A61M 25/0631* (2013.01)

(58) Field of Classification Search
CPC .......... A61M 25/0631; A61M 25/0618; A61M 25/0097
See application file for complete search history.

(56) References Cited

U.S. PATENT DOCUMENTS 3,335,723 A    8/1967    Waldman
3,352,306 A    11/1967    Hirsch
(Continued)

FOREIGN PATENT DOCUMENTS

EP    0993839    4/2000
JP    2006055674    3/2006
(Continued)

OTHER PUBLICATIONS

ISA; International Search Report and Written Opinion PCT Application No. PCT/US18/021135 dated May 16, 2018.
(Continued)

*Primary Examiner* — Jenna Zhang
(74) *Attorney, Agent, or Firm* — Louis Woo

(57) ABSTRACT

The present disclosure provides for a safety catheter assembly comprising a needle hub, a catheter hub, a tip protector housing. Various embodiments can comprise a push-off tab extending radially from the tip protector housing or a portion thereof, and/or structure can be added or removed to affect compliance between a catheter assembly and a catheter insertion device.

19 Claims, 9 Drawing Sheets

Related U.S. Application Data

(60) Provisional application No. 62/576,836, filed on Oct. 25, 2017, provisional application No. 62/467,397, filed on Mar. 6, 2017.

(56) References Cited

U.S. PATENT DOCUMENTS

| | | | |
|---|---|---|---|
| 4,755,356 A | 7/1988 | Robbins et al. | |
| 5,558,651 A | 9/1996 | Crawford et al. | |
| 5,645,539 A * | 7/1997 | Solomon | A61M 16/0825 |
| | | | 604/905 |
| 5,697,014 A | 12/1997 | Brimhall | |
| 5,810,780 A | 9/1998 | Brimhall et al. | |
| 6,497,994 B1 | 12/2002 | Kafrawy | |
| 6,527,747 B2 * | 3/2003 | Adams | A61M 25/0637 |
| | | | 604/162 |
| 7,597,681 B2 | 10/2009 | Sutton et al. | |
| 7,736,337 B2 | 6/2010 | Diep et al. | |
| 8,979,803 B2 | 3/2015 | Darr | |
| 2002/0026154 A1 * | 2/2002 | Chang | A61M 5/3273 |
| | | | 604/198 |
| 2002/0107483 A1 | 8/2002 | Cook | |
| 2003/0105431 A1 * | 6/2003 | Howell | A61M 5/3273 |
| | | | 604/164.08 |
| 2004/0215146 A1 | 10/2004 | Lampropoulos et al. | |
| 2004/0267200 A1 | 12/2004 | Carlyon et al. | |
| 2005/0015071 A1 | 1/2005 | Brimhall | |
| 2005/0075606 A1 | 4/2005 | Botich et al. | |
| 2008/0300543 A1 | 12/2008 | Abriles et al. | |
| 2010/0305519 A1 | 12/2010 | McKinnon et al. | |
| 2011/0054402 A1 | 3/2011 | Tanabe et al. | |
| 2011/0054403 A1 | 3/2011 | Tanabe et al. | |
| 2012/0136311 A1 | 5/2012 | Knutsson | |
| 2012/0323181 A1 | 12/2012 | Shaw et al. | |
| 2014/0303561 A1 * | 10/2014 | Li | A61M 5/1626 |
| | | | 604/164.08 |
| 2015/0151084 A1 | 6/2015 | Teoh | |
| 2016/0106959 A1 | 4/2016 | Woehr | |
| 2016/0220161 A1 | 8/2016 | Goral et al. | |
| 2016/0220791 A1 | 8/2016 | Akcay et al. | |
| 2016/0228683 A1 | 8/2016 | Tietze | |
| 2016/0310704 A1 | 10/2016 | Ng et al. | |
| 2016/0354539 A1 * | 12/2016 | Tan | A61M 5/158 |
| 2017/0120010 A1 | 5/2017 | Burkholz et al. | |
| 2017/0354799 A1 | 12/2017 | Gupta et al. | |
| 2018/0028788 A1 | 2/2018 | Belson | |
| 2018/0339131 A1 | 11/2018 | Muse et al. | |

FOREIGN PATENT DOCUMENTS

| | | |
|---|---|---|
| WO | 9614894 | 5/1996 |
| WO | 1999052584 | 10/1999 |
| WO | 2001056642 | 8/2001 |
| WO | 2002096494 | 12/2002 |
| WO | 2017074684 | 5/2017 |

OTHER PUBLICATIONS

ISA; International Search Report and Written Opinion PCT Application No. PCT/US18/021143 dated May 11, 2018.

ISA; International Search Report and Written Opinion PCT Application No. PCT/US18/021155 dated Apr. 27, 2018.

ISA; International Search Report and Written Opinion PCT Application No. PCT/US2020/021485 dated May 5, 2020.

ISA; International Preliminary Report on Patentability in PCT Application No. PCT/US2020/021485 dated Sep. 24, 2020.

EUIPO; Search Report dated Sep. 24, 2020 in EP Application No. 18763871.3.

EUIPO; Search Report dated Sep. 27, 2020 in EP Application No. 18764834.0.

USPTO; Non-Final Office Action dated Mar. 24, 2021 in U.S. Appl. No. 16/486,126.

USPTO; Non-Final Office Action dated Apr. 13, 2021 in U.S. Appl. No. 16/486,108.

USPTO; Non-Final Office Action dated Jul. 20, 2021 in U.S. Appl. No. 16/811,714.

USPTO; Notice of Allowance dated Aug. 6, 2021 in U.S. Appl. No. 16/486,108.

USPTO; Final Office Action dated Aug. 26, 2021 in U.S. Appl. No. 16/486,126.

Wang et al., Optimal Needle Design for Minimal Insertaion Force and Bevel Length, Medical Engineering and Physics 36, 2014 ( Year: 2014).

* cited by examiner

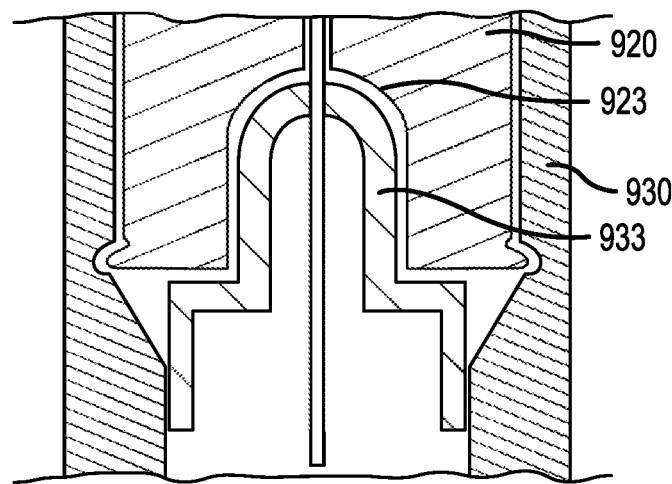
FIG.9C
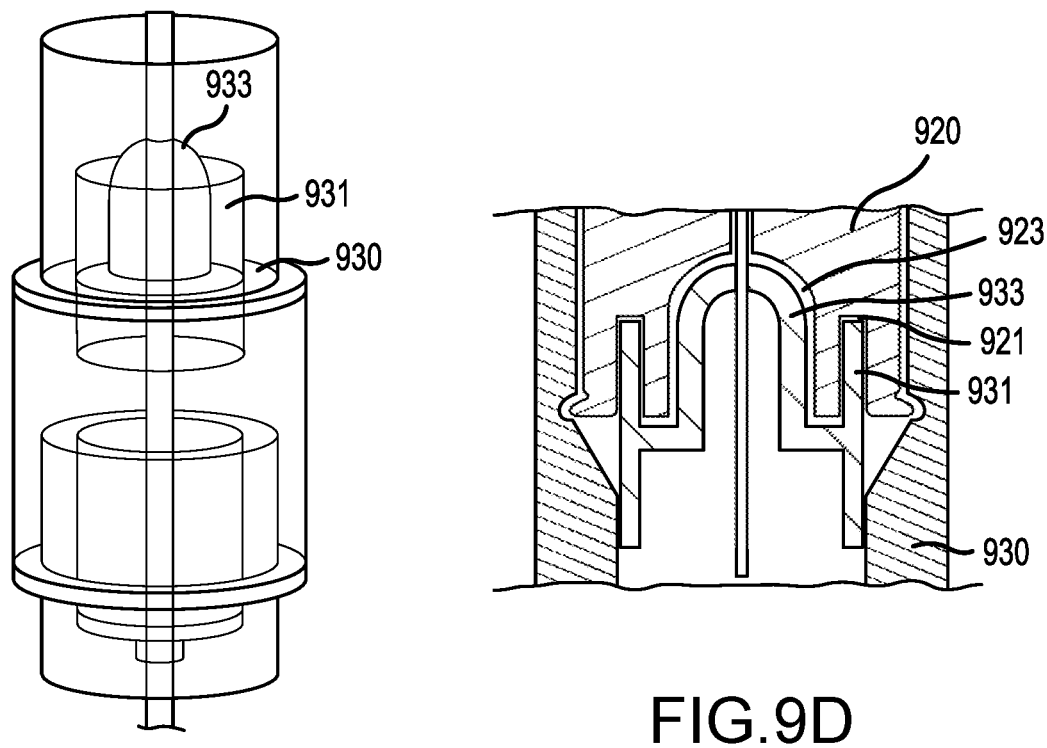
FIG.9D
FIG.9E

CATHETER INSERTION DEVICE WITH TIP PROTECTOR HOUSING

CROSS-REFERENCE TO RELATED APPLICATIONS

This application is a continuation of U.S. application Ser. No. 16/486,108 filed on Aug. 14, 2019 and entitled "CATHETER INSERTION DEVICE WITH TIP PROTECTOR HOUSING." The '108 application is the U.S. national phase filing under 35 U.S.C. § 371 of PCT/US2018/021135 (the "'135 application") filed on Mar. 6, 2018 and entitled "CATHETER INSERTION DEVICE WITH TIP PROTECTOR HOUSING." The '135 application claims priority to and the benefit of U.S. Ser. No. 62/467,397 filed on Mar. 6, 2017 and entitled "PERIPHERAL IV CATHETER," and U.S. Ser. No. 62/576,836 filed on Oct. 25, 2017 and entitled "CATHETER INSERTION DEVICE WITH TIP PROTECTOR HOUSING." All of the aforementioned disclosures are incorporated herein by reference in their entirety for all purposes.

BACKGROUND

Operators of safety catheter assemblies have historically been at risk of needle sticks. Various needle tip protectors are known in the art, however, separation of the needle tip protector from the catheter hub in connection with deployment presents challenges. For example, in some implementations, a push-off tab located on the catheter hub facilitates deployment, but becomes an obstruction post-deployment, when the catheter is in use. Making the push-off tab smaller in such implementations, so as to be less of an obstruction, makes it difficult for an operator to grip or otherwise actuate. In other implementations, there is a risk of premature separation of the needle tip protector from the catheter hub, particularly when a bending moment is introduced at or near their coupling and/or the needle is being withdrawn, thus undermining the desired protection against needle sticks.

Premature separation of the needle tip protector from the catheter hub may occur when excessive pressure is applied when gripping the needle hub with the needle tip protector positioned inside of the needle hub. Further, premature separation may occur in the event of excessive upward pull against the needle hub with the needle tip protector positioned inside of the needle hub. Still further, premature separation may occur in the event of excessive needle bend after the needle hub is pulled proximally of the needle tip protector.

BRIEF DESCRIPTION OF THE FIGURES

The accompanying drawings are included to provide a further understanding of the present disclosure and are incorporated in, and constitute a part of, this specification, illustrate various embodiments, and together with the description, they serve to explain the principles of the disclosure.

FIG. 9C illustrates a cross-sectional view of a tip protector housing comprising an extension in accordance with an embodiment of the present disclosure;

FIGS. 9D and 9E illustrate cross-sectional and perspective views, respectively, of a tip protector housing comprising a plurality of extensions in accordance with an embodiment of the present disclosure.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, mechanical and structural changes may be made without departing from the spirit and scope of the disclosure. Thus, the detailed description herein is presented for purposes of illustration only and not of limitation.

For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Any of the components may be coupled to each other via friction, snap, sleeves, brackets, clips or other means now known in the art or hereinafter developed. Additionally, any reference to without contact (or similar phrases) may also include reduced contact or minimal contact. As used herein, "proximal(ly)" refers to closer to the operator and further from the subject, while "distal(ly)" refers to further from the operator and closer to the subject.

Figure 1:
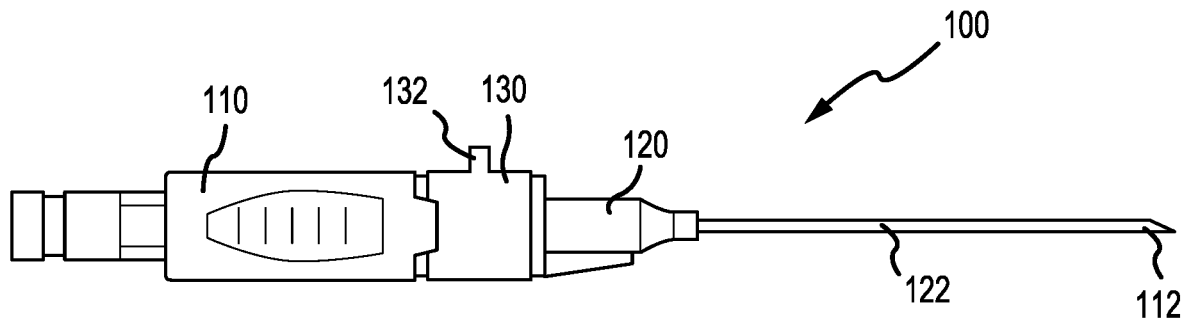
FIG. 1 illustrates an example embodiment of a safety catheter assembly.

With reference to FIG. 1, a safety catheter assembly 100 is disclosed herein. Example embodiments of safety catheter assembly 100 comprise a needle hub 110, a catheter hub 120, a tip protector housing 130, and a push-off tab 132 extending radially from tip protector housing 130 or a portion thereof. Needle hub 110, catheter hub 120, catheter 122, and tip protector housing 130 can each be comprised of materials now known in the art or hereinafter developed. A catheter hub and a catheter may be referred to together herein as a catheter assembly. A needle hub, a needle and a tip protector housing may be referred to together herein as a catheter insertion device.

As disclosed herein, needle hub 110 is a structure to which a needle 112 is connected or which otherwise secures needle 112. Needle 112 can extend distally from a distal end of needle hub 110. Needle 112 can be a conventional intravenous needle, a trocar or the like.

In accordance with the present disclosure, catheter hub 120 is a structure to which a catheter 122 is connected or which otherwise secures catheter 122. Catheter 122 can extend distally from a distal end of catheter hub 120. Catheter hub 120 and catheter 122 can each have a lumen extending there through, the lumen of catheter hub 120 being in communication with the lumen of catheter 122.

In example embodiments, tip protector housing 130 is positioned between needle hub 110 and catheter hub 120, and is configured to protect an operator from accidental needle sticks. In example embodiments, push-off tab 132 extends radially from tip protector housing 130, being either coupled to or integral with tip protector housing 130. In general, push-off tab 132 extends radially in a direction away from a skin surface, for example, on the side interfaced with by an operator. Push-off tab 132 can have a height, as measured from its base at tip protector housing 130, of more than about 2 mm, or more than about 4 mm, or more than about 6 mm.

Push-off tab 132 not located on catheter hub 120 can facilitate deployment while not being an obstruction post-deployment. In accordance with example embodiments of the present disclosure, push-off tab 132 can be located proximal to, coincident with, or distal to, a proximal end of catheter hub 120.

Push-off tab 132 can be configured to be comfortable for an operator when used correctly, and/or uncomfortable for an operator when used incorrectly. For example, a proximal side of push-off tab 132 can be smooth and ergonomically suited for being pressed by an operator's finger, while a distal side of push-off tab 132 can be rough or angled to discourage contact by an operator.

In example embodiments, needle hub 110 is adjacent, but not coupled, to tip protector housing 130. In such embodiment, there may be no overlap between a distal end of needle hub 110 and a proximal end of tip protector housing 130. In other example embodiments, a distal end of needle hub 110 is passively coupled to a proximal end of tip protector housing 130. The coupling can include sliding contact with a key and keyway or the like, for example, to prevent rotational relative movement, but not axial relative movement.

In example embodiments, tip protector housing 130 is removably coupled to catheter hub 120 by a coupling that separates when a threshold force is exceeded. Such threshold force couplings can include friction fit joints, a snap fit joints, or the like. For example, a proximal end of catheter hub 120 may comprise a snap groove that removably interfaces with a snap ring on a distal end of tip protector housing.

Safety catheter assembly 100 as described herein has at least three positions. In a ready position, at least a portion of needle 112 extends through catheter 122, and a distal tip of needle 112 extends beyond a tip of catheter 122. In the ready position, a distal end of tip protector housing 130 is temporarily coupled to a proximal end of catheter hub 120.

In a safe position, catheter 122 and needle 112 (and catheter hub 120 and needle hub 110) have been moved relative to each other such that no portion of needle 112 extends through catheter 122, and the distal tip of needle 112 is securely housed within tip protector housing 130 (e.g., with or without structure being displaced in front of the distal tip of needle 112), so as to provide protection against accidental needle sticks. In the safe position, distal end of tip protector housing 130 is still temporarily coupled to proximal end of catheter hub 120.

Finally, in a released position, the distal tip of needle 112 is housed within tip protector housing 130, and distal end of tip protector housing 130 is released from proximal end of catheter hub 120.

Figure 2A:
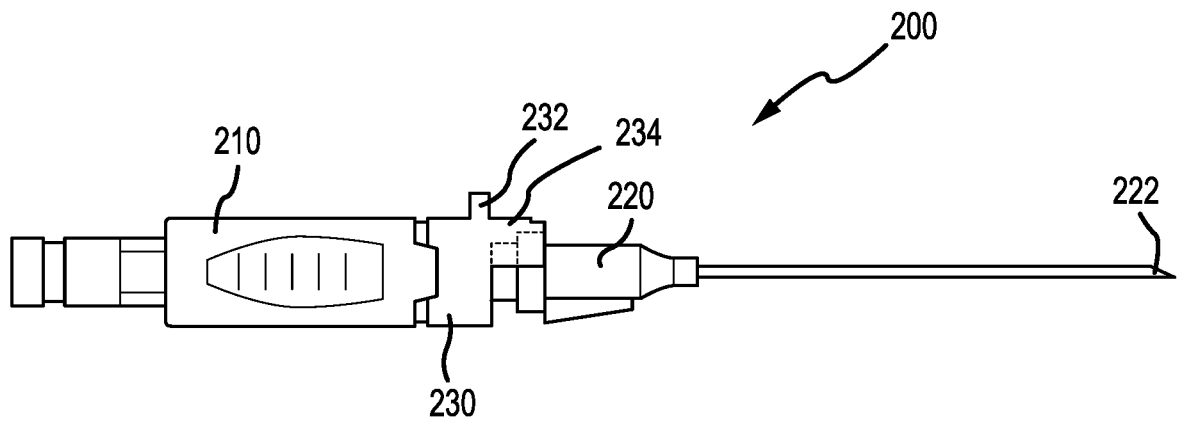
FIGS. 2A and 2B illustrate side views of an example embodiment of a safety catheter assembly, in ready and released positions, respectively.
Figure 2B:
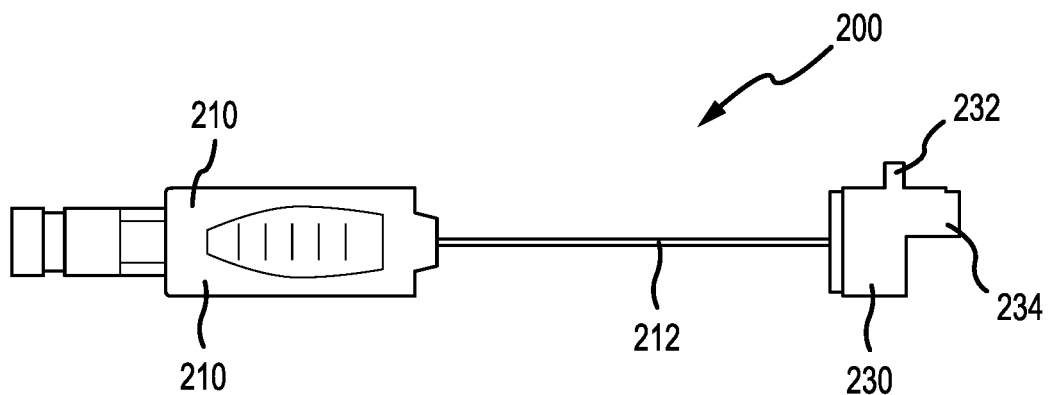

A safety catheter assembly 200 in accordance with another embodiment of the present disclosure will now be described with reference to FIGS. 2A and 2B. Safety catheter assembly 200 is shown in a ready position in FIG. 2A, and a portion of safety catheter assembly 200 is shown in a released position in FIG. 2B. A needle hub 210 has a needle 212 extending from a distal end of needle hub 210. A catheter hub 220 has a catheter 222 extending from a distal end of catheter hub 220. A tip protector housing 230 is located between needle hub 210 and catheter hub 220. A push-off tab 232 extends radially from tip protector housing 230.

In the illustrated embodiment, tip protector housing 230 comprises a tab extension 234 extending distally over at least a portion of catheter hub 220, for example, over more than about 20 percent, or about 30 percent, or about 50 percent, of the overall length of catheter hub 220.

In the example embodiment, the overlap of tip protector housing 230 does not diminish any contact between catheter hub 220 and a skin surface. By way of non-limiting example, tab extension 234 can be located exclusively on the side of safety catheter assembly 200 interfaced with by an operator. In example embodiments, the overlap of tip protector housing 230 may absorb all or a portion of a bending moment at the coupling between catheter hub 220 and tip protector housing 230. In this regard, the overlap of tip protector housing 230 may prevent premature separation of tip protector housing 230 from the catheter hub 220.

Tab extension 234 can comprise a substantially flat profile or a curved profile (e.g., concave toward catheter hub 220) that substantially wraps over or otherwise follows the curvature of the overlapped portion of catheter hub 220. Tab extension 234 having a flat profile in example embodiments can have a width smaller than, about equal to, or greater than the diameter of catheter hub 220. Example embodiments of tab extension 234 having a curved profile can wrap about the catheter hub 220 by differing amounts, such 60 degrees or greater, 120 degrees or greater, 180 degrees or greater, or even up to 270 degrees or greater.

In example embodiments, push off-tab 232 extends radially from tab extension 234 of tip protector housing 230, push off-tab 232 being either coupled to or integral with tab extension 234. In example embodiments, push-off tab 232 is located over a portion of catheter hub 220 (i.e., push-off tab 232 is located distal to a proximal end of catheter hub 220). Positioning push-off tab 232 above catheter hub 220 may also direct forces along the axis of needle 212, which can prevent side loading and bending moments at the coupling between catheter hub 220 and tip protector housing 230.

A safety catheter assembly 300 in accordance with the present disclosure will now be described with reference to FIGS. 3A-3D. Safety catheter assembly 300 is shown in a ready position in FIGS. 3A-3C, and a portion of safety catheter assembly 300 is shown in a released position in FIG. 3D. A needle hub 310 has a needle 312 extending from a distal end of needle hub 310. A catheter hub 320 has a catheter 322 extending from a distal end of catheter hub 320. A tip protector housing 330 is located between needle hub 310 and catheter hub 320. A push-off tab 332 extends radially from tip protector housing 330.

In example embodiments, tip protector housing 330 is at least partially housed within or enclosed by needle hub 310 when in the ready position. In this regard, at least a portion of tip protector housing 330 has a diameter (or other cross section) smaller than at least a portion of needle hub 310. In example embodiments, needle hub 310 comprises a window 314 through which push-off tab 332 radially extends from tip protector housing 330. Stated another way, tip protector housing 330 can be substantially housed within or enclosed by needle hub 310, except for window 314 in needle hub 310 through which push-off tab 332 extends and is accessible. In example embodiments, and with momentary reference to FIG. 3D, needle hub 310 comprises a plurality of windows 314, for example on opposing sides of needle hub 310. Window 314 generally extends from, and is open to, a distal end of needle hub 310.

Figure 3A:
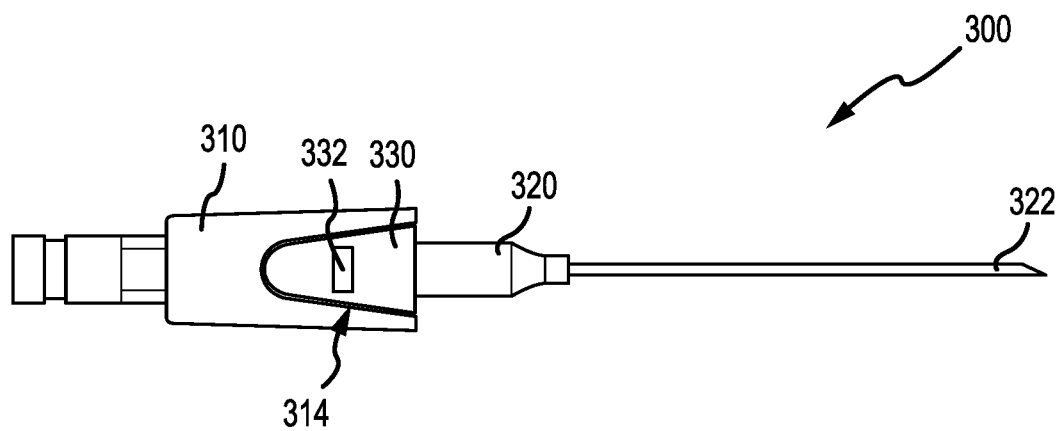
FIGS. 3A and 3B illustrate top and side views, respectively, of another example embodiment of a safety catheter assembly in a ready position.
Figure 3B:
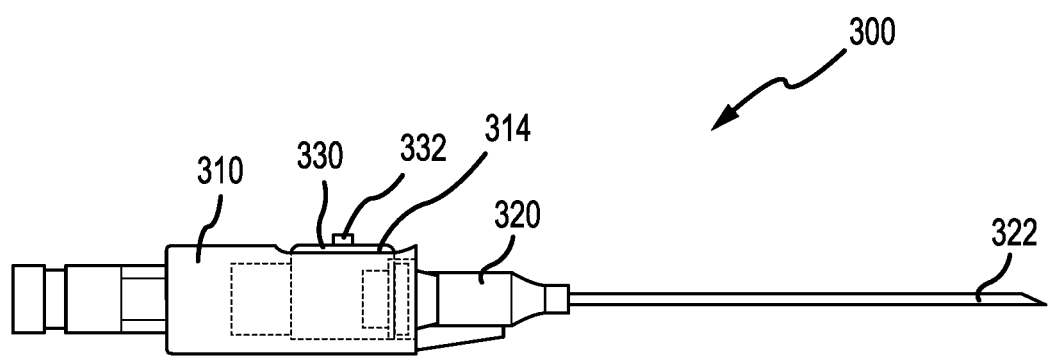

In example embodiments, a distal end of tip protector housing 330 substantially coincides with a distal end of needle hub 310 (e.g., with reference to FIGS. 3A and 3B). Stated differently, tip protector housing 330 is completely circumferentially enclosed within needle hub 310 (except for push-off tab 332) in example embodiments, such that a distal end of needle hub 310 is adjacent to a proximal end of catheter hub 320. In such embodiments, the distal end of needle hub 310 and a proximal end of catheter hub 320 may not overlap.

Figure 3C:
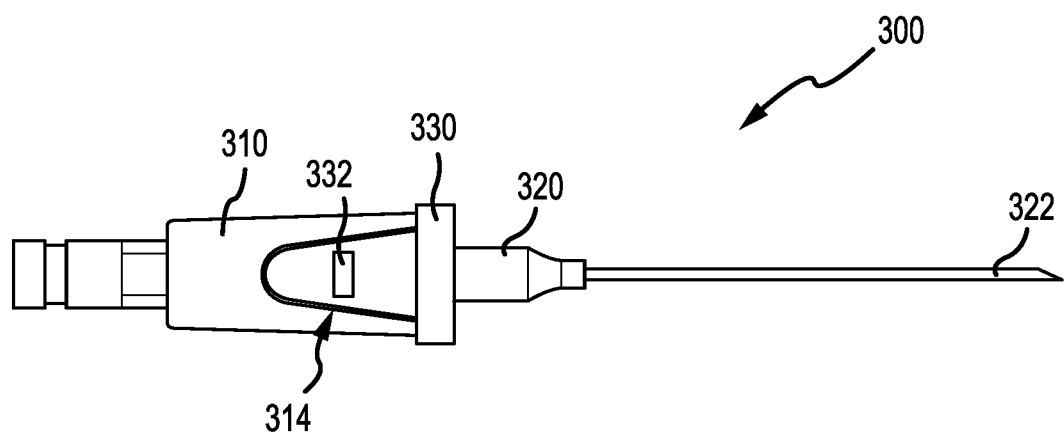
FIGS. 3C and 3D illustrate top views of yet another example embodiment of a safety catheter assembly, in ready and released positions, respectively.
Figure 3D:
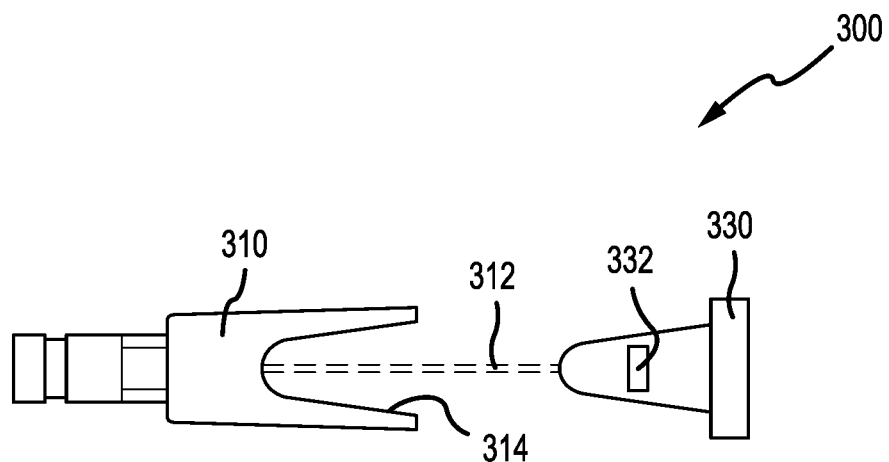

In other embodiments, a distal end of tip protector housing 330 extends distal to a distal end of needle hub 310 (e.g., with reference to FIGS. 3C and 3D). In example embodiments, push-off tab 332 is not located over any portion of catheter hub 320 (i.e., push-off tab 332 is located coincident with or proximal to a proximal end of catheter hub 320).

In still other embodiments, a tip protector housing can be completely circumferentially housed within a needle hub, except for a tab extension as described with reference to FIGS. 2A and 2B, from which a push-off tab extends radially for an operator to grip or otherwise actuate. Such embodiment may be particularly beneficial in terms of shortening the overall length of the safety catheter assembly.

The present disclosure contemplates additional embodiments configured to lessen the risk of premature separation between the catheter assembly and the catheter insertion device.

As described above, a safety catheter assembly can comprise a catheter assembly and a catheter insertion device. The catheter assembly can comprise a catheter hub and a catheter extending distally from the catheter hub. The catheter insertion device can comprise a needle hub, a needle extending distally from the needle hub along a longitudinal axis and having a sharp distal tip, and a tip protector housing.

In various embodiments, at least a portion of each of the catheter hub and the tip protector housing can define a coupling. In some embodiments, the coupling can be constructed and/or arranged to couple the catheter insertion device to the catheter. In some embodiments, the coupling can be configured to selectively release the catheter insertion device from the catheter when a threshold release force applied proximally along the longitudinal axis is exceeded. A threshold release force, in accordance with the present disclosure, can be below about 0.75 pounds force, or between about 0.75 and 0.25 pounds force, for example, about 0.7, 0.6, 0.5, 0.4 or 0.3 pounds force.

In some embodiments, the coupling can be configured to prevent release of the catheter insertion device from the catheter responsive to forces applied laterally to the longitudinal axis.

In various embodiments, in a ready position, the needle extends through the catheter of the catheter assembly and the tip protector housing is coupled to the catheter hub through the coupling. From the ready position in accordance with the present disclosure, retraction of the needle relative to the catheter along the longitudinal axis moves the catheter insertion device to a safe position with the sharp distal tip of the needle housed within the tip protector housing and the tip protector housing coupled to the catheter hub through the coupling. From the safe positon in accordance with the present disclosure, further retraction of the needle along the longitudinal axis with a force in excess of a release force moves the catheter insertion device to a released position with the needle separated from the catheter, the distal tip of the needle housed within the tip protector housing and the tip protector housing released from the catheter hub.

In general, the risk of premature separation can be lessened by incorporating structure to increase compliance between a catheter assembly as described herein (or a portion thereof, e.g., a catheter hub) and a catheter insertion device as described herein (or a portion thereof, e.g., a tip protector housing).

Figure 4:
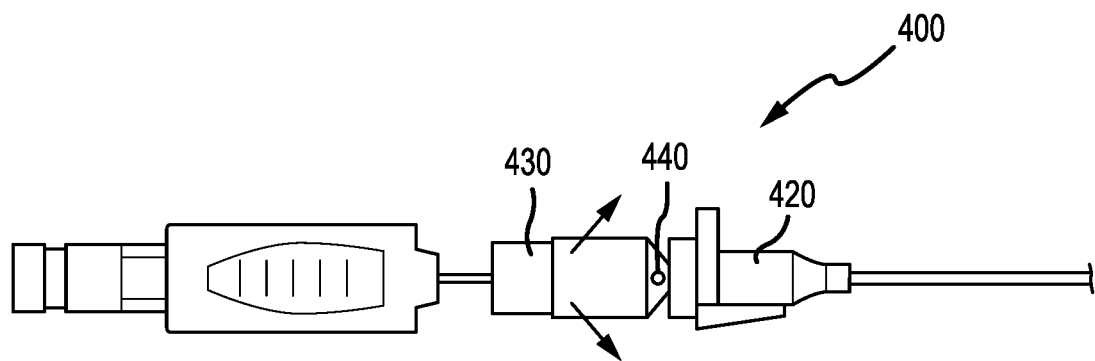
FIG. 4 illustrates a safety catheter assembly comprising a pivoting joint in accordance with an embodiment of the present disclosure.

With reference to FIG. 4, a safety catheter assembly 400 can comprise a coupling defined by at least a portion of each of a catheter hub 420 and a tip protector housing 430. The coupling can comprise a pivoting joint 440 that allows tip protector housing 430 to pivot or rotate relative to catheter hub 420 and away from the longitudinal axis of safety catheter assembly 400, and do so in the direction shown by the arrows. Pivoting joint 440 can comprise protrusions on the inside of tip protector housing 430 that are received in dimples on the outside of catheter hub 420, or vice versa.

Figure 5:
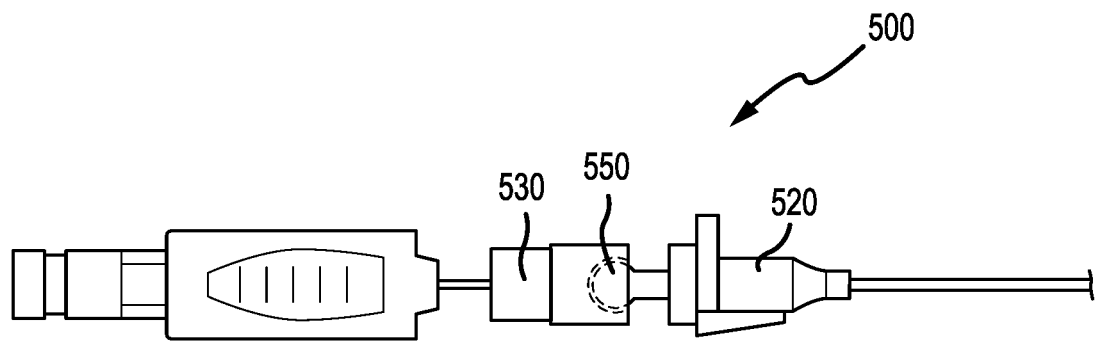
FIG. 5 illustrates a safety catheter assembly comprising a ball joint in accordance with an embodiment of the present disclosure.

Turning to FIG. 5, a safety catheter assembly 500 can comprise a coupling defined by at least a portion of each of a catheter hub 520 and a tip protector housing 530. The coupling can comprise a ball joint 550 that allows tip protector housing 530 to pivot or rotate relative to catheter hub 520 and away from the longitudinal axis of safety catheter assembly 500, and do so in a plurality of directions.

Figure 6:
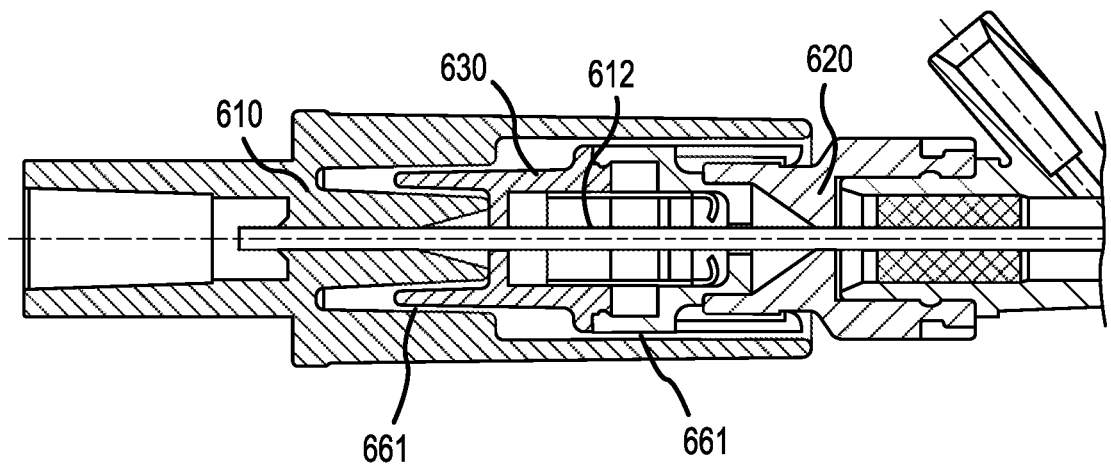
FIG. 6 illustrates a cross-sectional view of a safety catheter assembly in accordance with an embodiment of the present disclosure.

With reference to FIG. 6, an amount of clearance 661 between an interior surface of a needle hub 610 and an exterior surface of a tip protector housing 630 can provide space for movement of needle hub 610 relative to tip protector housing 630 to thereby permit a needle 612 to bend with a decreased risk of premature separation between a catheter hub 620 and tip protector housing 630.

Figure 7:
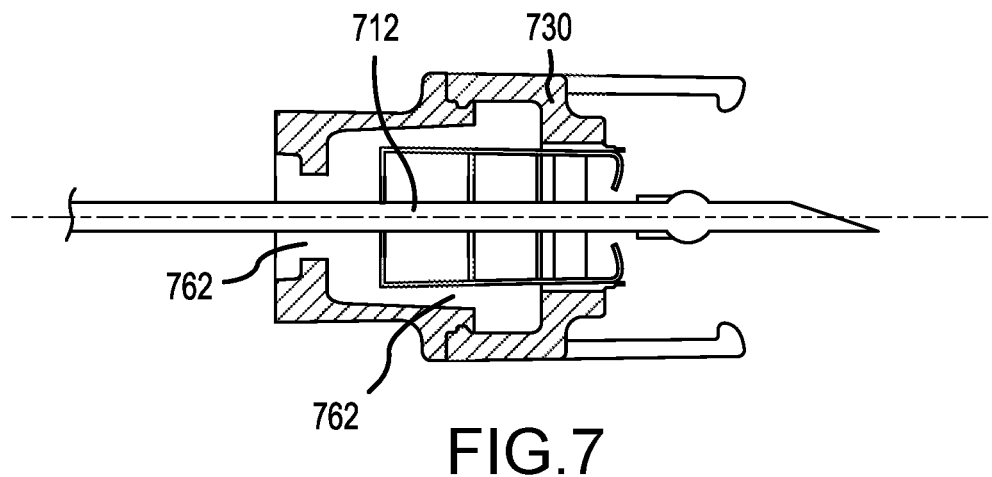
FIG. 7 illustrates yet another cross-sectional view of a safety catheter assembly in accordance with an embodiment of the present disclosure.

Similarly, and with reference now to FIG. 7, an amount of clearance 762 between an interior surface of a tip protector housing 730 and a needle 712 can provide space for needle 712 to bend with a decreased risk of premature separation between a catheter hub and tip protector housing 730. In this regard, needle 712 may be allowed to bend without initially contacting the tip protector housing, either directed or through the tip protector.

In still other embodiments, the risk of premature separation can be lessened by incorporating structure to decrease compliance between a catheter assembly as described herein (or a portion thereof, e.g., a catheter hub) and a catheter insertion device as described herein (or a portion thereof, e.g., a tip protector housing).

As a non-limiting example, a needle hub can comprise a stiffness sufficient to resist temporary deformation by a user during use, such as when gripped with excessive forces by a user. This may be accomplished by molding the needle hub from a stiffer material. Additionally or alternatively, the needle hub design may be altered to create a stiffer structure, such as with the addition of ribs, thicker walls and the like.

As another non-limiting example, an amount of clearance between an interior surface of a needle hub and an exterior surface of a catheter hub can be lessened. Stated differently, an interior surface of a needle hub and an exterior surface of a catheter hub can be in close contact or proximity to one another. In this regard, the risk of premature separation between the catheter hub and a tip protector housing can be lessened.

In various embodiments of the present disclosure, one or more contact points between the catheter hub and the tip protector housing can counter forces that may cause unintended separation at a coupling defined by at least a portion of each of a catheter hub and a tip protector housing. The orientation of the contact point(s) relative to the anticipated bending moment(s) can further counter forces that may cause unintended separation.

Figure 8:
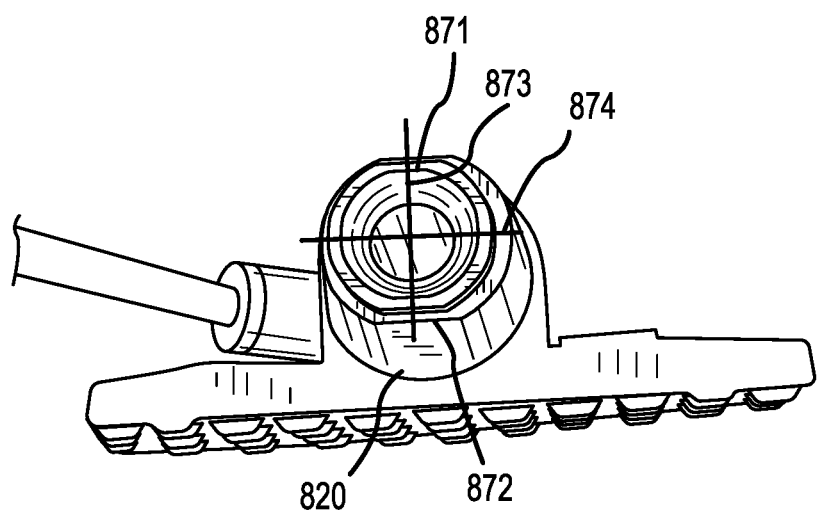
FIG. 8 illustrates contact points at a coupling of a safety catheter assembly in accordance with an embodiment of the present disclosure.

In this regard, and with reference now to FIG. 8, a coupling can comprise a first contact point 871 between a catheter hub 820 and a tip protector housing oriented at 0 degrees and a second contact point 872 between catheter hub 820 and the tip protector housing oriented at 180 degrees. In general, the location of one or more contact points can be selected such that moments about a vertical plane 873 are resisted more than moments about a horizontal plane 874. In such embodiments, forces that may cause unintended separation may be countered, while not necessarily increasing the force required to intentionally separate catheter hub 820 from the tip protector housing.

Figure 9A:
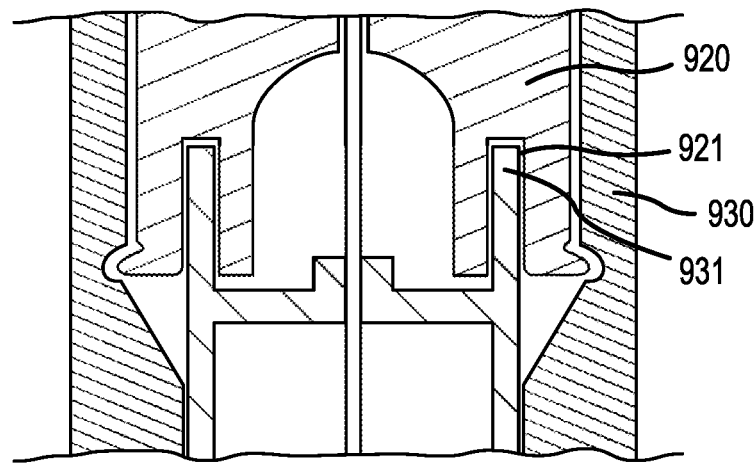
FIGS. 9A and 9B illustrate cross-sectional and perspective views, respectively, of a tip protector housing comprising an extension in accordance with an embodiment of the present disclosure.
Figure 9B:
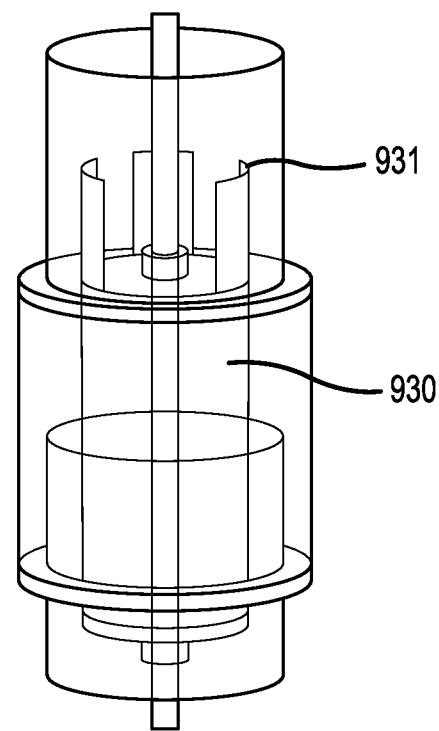

In various embodiments, and with reference to FIGS. 9A and 9B, a tip protector housing 930 can comprise an extension 931 coupled to a distal portion of tip protector housing 930 and received within a groove or recess of a proximal portion 921 of a catheter hub 920 when the safety catheter assembly is in both a ready position and a safe position. Extension 931 can be constructed as a solid, cylindrical structure (as best illustrated in FIG. 9E), or comprise a plurality of tabs arranged in a circular orientation (as best illustrated in FIG. 9B). Extension 931 may have a shape other than circular. Groove or recess of proximal portion 921 can generally correspond to extension 931, for example, to permit coupling of catheter hub 920 with tip protector housing 930 only when rotated relative to each other in a desired orientation.

Similarly, and with reference to FIG. 9C, a tip protector housing 930 can comprise a dome extension 933 coupled to a distal portion of tip protector housing 930 and received within a recess of a proximal portion 923 of a catheter hub 920. Recess of proximal portion 923 can generally correspond to dome extension 933.

With reference now to FIGS. 9D and 9E, a tip protector housing 930 can comprise extensions 931, 933 coupled to distal portions of tip protector housing 930 and received within grooves or recesses of proximal portions 921, 923 of a catheter hub 920.

Figure 10A:
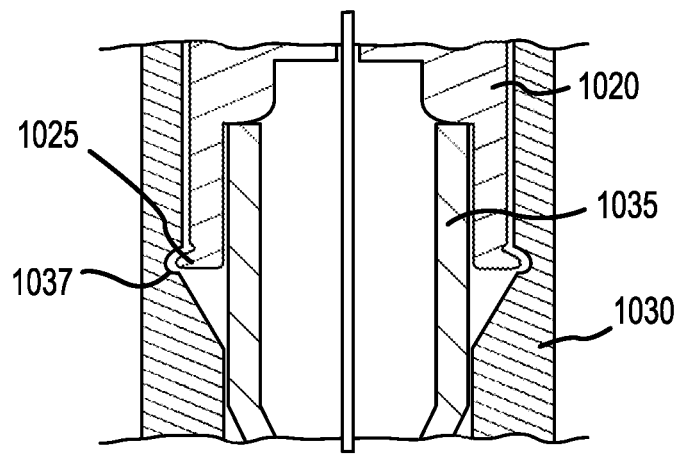
FIGS. 10A and 10B illustrate locked and unlocked positons, respectively, of a safety catheter assembly comprising an lock sleeve in accordance with an embodiment of the present disclosure.
Figure 10B:
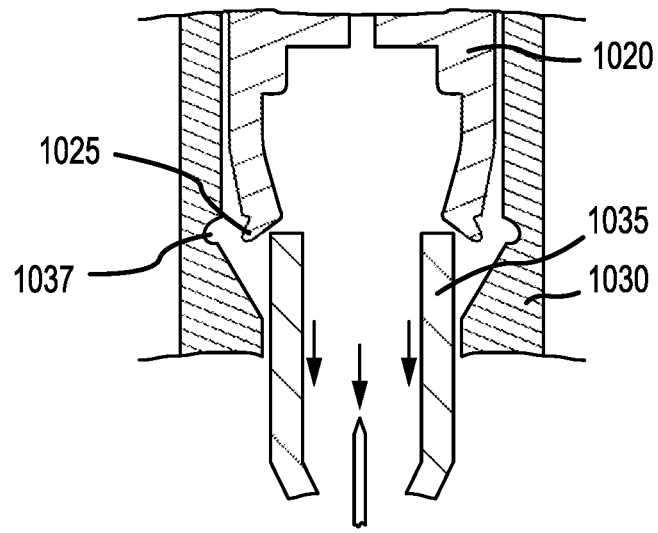

In various embodiments of the present disclosure, and with reference to FIGS. 10A and 10B, a catheter insertion device can comprise a lock sleeve 1035. Lock sleeve 1035 can be moveable within a tip protector housing 1030 from a locked position (FIG. 10A) in which lock sleeve 1035 is positioned at least partially within a proximal portion of a catheter hub 1020 in the direction shown by the arrows to an unlocked position (FIG. 10B) in which lock sleeve 1035 is not positioned within a proximal portion of catheter hub 1020.

In the locked position, lock sleeve 1035 may prevent inward movement of a tab 1025 on catheter hub 1020 from a gap 1037. Gap 1037 and tab 1025 can each be circumferential or at discrete positions around the circumference of tip protector housing 1030 and catheter hub 1020, respectively. Gap 1037 and tab 1025 can combine to form a snap fit joint.

In the unlocked position, lock sleeve 1035 may no longer prevent inward movement of tab 1025 from a gap 1037 such that tab 1025 no longer prevents separation of a coupling defined by at least a portion of each of catheter hub 1020 and tip protector housing 1030.

Lock sleeve 1025 may be formed as an integral part of the tip protector or may be a separate component that is connected to or acted on by the tip protector to move lock sleeve 1025 proximally. According to some examples, the lock sleeve may include features that are positioned proximally of the proximal end of the tip protector. In this respect, lock sleeve 1025 will be pulled proximally to the unlocked position by the tip protector, when the tip protector is acted on by a bump on a needle.

In other example embodiments of the present disclosure, a lock sleeve (or similar type mechanisms) is rotatable relative to a tip protector housing and/or catheter hub to move between a locked and an unlocked position. Helical or ramped features may be formed directly in the needle shaft. During needle withdrawal as the needle is pulled proximally, these helical features or ramps can act to rotate a lock sleeve to cause disengagement of the tip protector housing and the catheter hub. The ramp features may be formed directly on the metal material of the needle shaft. Alternatively, a separate component that includes the helical or ramp features may be secured to the needle shaft, such as with an adhesive. Including the helical or ramp features in a separate component may allow the helical/ramp features to be positioned in greater radial distance from the central needle axis, thus providing for greater mechanical advantage in moving the lock sleeve from the locked positon to the unlocked positon.

In example embodiments of the present disclosure, a coupling defined by at least a portion of each of catheter hub 1020 and tip protector housing 1030 provides an overlap between tip protector housing 1030 and catheter hub 1020. The distance of overlap, taken in a direction that extends distally to proximally, can be increased to provide greater resistance to bending moments or side loads that may cause premature separation.

Persons skilled in the art will appreciate that the foregoing embodiments comprising an lock sleeve may be used in connection with other embodiments described herein, for example, with reference to FIGS. 9A, 9C and 9D, which illustrate tabs and gaps similar to those described above.

It will be apparent to those skilled in the art that various modifications and variations can be made in the present disclosure without departing from the spirit or scope of the disclosure. For example, while various embodiments have been described with reference to safety catheter assemblies, the invention is not so limited. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

The invention claimed is:

1. A safety catheter assembly, comprising:
    a catheter hub having a distal end from which a catheter having a distal end extends distally and a proximal end;
    a catheter insertion device including:
        a needle hub having a distal portion with a distal end from which a needle having a distal tip extends distally;
        a tip protector housing having a proximal end and a distal end, the distal end of the needle hub and the distal end of the tip protector housing substantially coincides with each other such that the tip protector housing is completely enclosed within the needle hub except for a window at the needle hub through which a push-off tab extends radially from the tip protector housing, the distal end of the tip protector housing adapted to be removably coupled to the proximal end of the catheter hub;
    wherein the safety catheter assembly is in a ready position when the tip protector housing and the catheter hub are coupled together by a coupling such that the needle extends through the catheter hub and the catheter, the distal tip of the needle extends beyond the distal end of the catheter and the push-tab at the tip protector housing is accessible to facilitate the deployment of the safety catheter assembly.

2. The safety catheter assembly of claim 1, wherein the coupling comprises a ball or pivot joint that allows the tip protector housing to pivot or rotate relative to the catheter hub in a plurality of directions.

3. The safety catheter assembly of claim 1, wherein an amount of clearance between an interior surface of the needle hub and an exterior surface of the tip protector housing, or an amount of clearance between an interior surface of the tip protector housing and the needle, provides space for the needle to bend.

4. The safety catheter assembly of claim 1, wherein the coupling comprises a lock sleeve moveable proximally within the tip protector housing from a locked position, in which the lock sleeve is positioned at least partially within a proximal portion of the catheter hub, to an unlocked position, in which the lock sleeve is not positioned within the proximal portion of the catheter hub.

5. The safety catheter assembly of claim 4, wherein the lock sleeve is rotatable relative to the tip protector housing.

6. The safety catheter assembly of claim 1, wherein the coupling comprises a lock sleeve within the tip protector housing movable to be at least partially positioned within a proximal portion of the catheter hub to prevent inward movement of a circumferential tab at the catheter from a circumferential gap at the inner wall of the tip protector housing.

7. The safety catheter assembly of claim 1, wherein the tip protector housing comprises a distal portion having at least one extension and the proximal portion of the catheter hub comprises at least one recess for receiving the at least one extension when the tip protector housing and the catheter hub are coupled to each other.

8. The safety catheter assembly of claim 1, wherein the tip protector housing comprises a distal portion and an inner wall, a distally extending sleeve at the distal portion, and a circumferential gap at the inner wall of the distal portion;
    wherein a circumferential tab is provided at the proximal end of the catheter hub; and
    wherein when the tip protector housing and the catheter hub are coupled together, the sleeve is at least partially positioned within a proximal portion of the catheter hub to prevent inward movement of the circumferential tab from the circumferential gap.

9. The safety catheter assembly of claim 1, wherein the coupling is configured to couple the catheter insertion device and the catheter hub together and to prevent release of the catheter insertion device from the catheter hub in response to forces applied laterally to the catheter, the catheter hub released from the catheter insertion device when a release force greater than the threshold of the forces holding the catheter hub and the catheter insertion device together is applied to separate the catheter hub from the catheter insertion device.

10. The safety catheter assembly of claim 1, wherein the tip protector housing has a diameter smaller than at least a portion of the needle hub such that the tip protector housing is circumferentially enclosed within the needle hub except for the window at the needle hub.

11. A safety catheter assembly adapted to be operable in at least a ready position and a safe position, comprising:
    a needle hub having a distal portion and a distal end at the distal portion from which a needle having a distal tip extends;
    a catheter hub having a proximal end and a distal end from which a catheter having a distal end extends;
    a tip protector housing having a proximal end and a distal end positioned between the needle hub and the catheter hub, the proximal end of the tip protector housing adapted to be removably coupled with the distal end of the needle hub and be enclosed by the distal portion of the needle hub, the distal end of the tip protector housing adapted to be removably coupled to the proximal end of the catheter hub, the tip protector housing further having a push-off tab extending radially from the tip protector housing in a direction away from a skin surface, the push-off tab having a proximal side ergonomically suited for being pressed by a finger;
    wherein the safety catheter assembly is in the ready position when the proximal end of the tip protector housing is in contact with the needle hub and the distal end of the tip protector housing is in contact with the catheter hub, and the distal tip of the needle extends beyond the distal end of the catheter;
    wherein the safety needle assembly is in the safe position when the needle hub is separated from the proximal end of the tip protector housing and the distal tip of the needle is captured in the tip protector housing, and when the catheter hub is removable from the tip protector housing, and wherein the tip protector housing includes a tab extension extending distally over at least a proximal portion of the catheter hub such that the push-off tab is adapted to be located over a portion of the catheter hub.

12. The safety catheter assembly of claim 11, wherein the tip protector housing is at least partially enclosed within the needle hub, and wherein the push-off tab extends through a window in the needle hub.

13. The safety catheter assembly of claim 11, wherein the push-off tab extends radially from a tab extension of the tip protector housing that extends distally over at least a proximal portion of the catheter hub such that the push-off tab is located proximal to the proximal end of the catheter hub.

14. The safety catheter assembly of claim 11, further comprising a window that opens from the distal end of the needle hub such that at least a proximal portion of the tip protector housing is adapted to be enclosed by the needle hub with the push-off tab extending through the window in the ready position.

15. The safety catheter assembly of claim 11, wherein the tip protector housing comprises a tab extension configured to overlap at least the proximal end of the catheter hub when the tip protector housing and the catheter hub are coupled to each other.

16. The safety catheter assembly of claim 11, wherein the tab extension has a substantially flat profile that overlaps at least a portion of the proximal portion of the catheter hub when the tip protector housing and the catheter hub are coupled to each other.

17. The safety catheter assembly of claim 11, wherein the tab extension has a curve profile that wraps about at least a proximal portion of the catheter hub when the tip protector housing and the catheter hub are coupled to each other.

18. The safety catheter assembly of claim 11, wherein the tip protector housing comprises a distal portion having at least one extension and the proximal portion of the catheter hub comprises at least one recess for receiving the at least one extension when the tip protector housing and the catheter hub are coupled to each other.

19. The safety catheter assembly of claim 11, wherein the tip protector housing comprises a distal portion having at least an inner wall, a distally extending sleeve at the distal portion and a gap at the inner wall of the distal portion;
wherein a circumferential tab is provided at the proximal end of the catheter hub; and
wherein when the tip protector housing and the catheter hub are in a locked position, the sleeve is at least partially positioned within a proximal portion of the catheter hub to prevent inward movement of the circumferential tab from the gap.

* * * * *